(12) United States Patent
Kolberg et al.

(10) Patent No.: US 9,014,817 B2
(45) Date of Patent: Apr. 21, 2015

(54) ELECTRODE CABLE WRAP

(75) Inventors: Gernot Kolberg, Berlin (DE); Thomas Doerr, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 13/359,930

(22) Filed: Jan. 27, 2012

(65) Prior Publication Data

US 2012/0203315 A1    Aug. 9, 2012

Related U.S. Application Data

(60) Provisional application No. 61/439,381, filed on Feb. 4, 2011.

(51) Int. Cl.
*H01R 13/60* (2006.01)
*A61N 1/375* (2006.01)
*H01R 13/72* (2006.01)

(52) U.S. Cl.
CPC .............. *H01R 13/60* (2013.01); *A61N 1/3752* (2013.01); *A61N 1/375* (2013.01); *H01R 13/72* (2013.01)

(58) Field of Classification Search
CPC ....... A61N 1/375; A61N 1/3752; H01R 13/72
USPC ...................................... 607/36–38
See application file for complete search history.

(56) References Cited

U.S. PATENT DOCUMENTS 4,094,321 A * 6/1978 Muto ............................. 607/36
4,266,552 A   5/1981 Dutcher et al.
5,107,836 A * 4/1992 Fenster ........................... 607/36
5,456,698 A * 10/1995 Byland et al. .................... 607/36
7,454,251 B2 * 11/2008 Rezai et al. .................... 607/115
7,769,443 B2 * 8/2010 Barolat ............................. 607/3
8,209,016 B2 * 6/2012 Deininger et al. .............. 607/36
2007/0179552 A1   8/2007 Dennis et al.
2008/0058876 A1   3/2008 Barolat

OTHER PUBLICATIONS

European Search Report and Notes to the European Search Report on European Patent Application No. EP 12 15 0659, dated May 10, 2012 (6 pages).

* cited by examiner

*Primary Examiner* — George Evanisko
(74) *Attorney, Agent, or Firm* — Buchanan Ingersoll & Rooney PC

(57) ABSTRACT

An implantable device for the reversible accommodation of an electrode lead portion of at least one electrode lead, including a first outer surface and a second outer surface which extends parallel to the first outer surface at a distance therefrom, the first outer surface having at least one guide which can be used to guide and accommodate the portion of the electrode lead. According to a second aspect, the electromedical implant includes the above-described device and an electronic circuit with a power supply, a multipiece housing which hermetically seals the circuit and the power supply, and a connector housing which is fastened to the multipiece, hermetically sealed housing and has connectors for at least one electrode lead, the connectors being electrically connected to the electronic circuit. The electromedical implant is characterized in that the second outer surface of the device is integrated into and forms a part of the housing.

16 Claims, 3 Drawing Sheets

ELECTRODE CABLE WRAP

RELATED APPLICATION

This patent application claims the benefit of U.S. Provisional Patent Application No. 61/439,381, filed on Feb. 4, 2011, which is hereby incorporated by reference in its entirety.

TECHNICAL FIELD

The presently claimed invention relates to an implantable device for the reversible accommodation of an electrode lead portion of at least one electrode lead for storing this electrode lead portion in a tissue or implant pocket in which an electromedical implant is implanted.

BACKGROUND

Electromedical implants typically comprise:
an electronic circuit with a power supply,
a multipiece housing which hermetically seals the electronic circuit and the power supply, and
a connector housing which is fastened to the multipiece, hermetically sealed housing and comprises connectors for at least one electrode lead, the connectors being electrically connected to the electronic circuit.

Such implants are typically used to induce a therapeutic effect at certain sites in the body after the need for this therapy has been identified, e.g., by way of a diagnostic function in the electromedical implant. The electromedical implants can be, for example, cardiac pacemakers, implantable defibrillators or cardioverters, nerve stimulators, and/or brain stimulators, among other things. Recently, such electromedical implants have also been used to receive endogenous signals which are collected in the implant and can be evaluated or transmitted to an external device for evaluation. This technique of "telemetry" is now commonly used in all electromedical implants, and therefore the other stated implants can also be provided with such a functionality.

As mentioned above, electromedical implants generally comprise a connector housing which is fastened to a multipiece, hermetically sealed housing and has connectors for at least one electrode lead. Such an electrode lead is generally comprised of an elongated body, the exterior of which is comprised of an insulating material such as, for example, silicone or polyurethane and the like. The body has a proximal end and a distal end. Situated on the proximal end is at least one plug connector which can be connected to the connector—typically a socket—in the connector housing. The plug is generally standardized and can be designed according to one of the standards such as IS-1, IS-4, or DF-1. Each of the electrically active contacts of the plug is electrically connected to a connecting line which is typically located on or in the vicinity of the distal end of each electrically active surface. Each of these connecting lines is insulated. The electrically active surfaces—which are also referred to in short as "electrode"—are used to induce electrical therapy at the body part to be treated (such as in or on the heart, or on nerves, etc.), or to receive measurement signals for diagnostic purposes.

Electrode leads are typically offered in various lengths. Three discrete lengths of cardiac electrode leads are currently available, for example. The implanting physician must therefore estimate which length is suitable for the particular patient and then select the length of electrode lead that fits as well as possible along the estimated length. Since there are only three lengths currently available, the electrode lead is generally more or less too long. Since the physician is unable to shorten the electrode lead and thereby tailor it to the patient, he typically wraps the excess portion on the proximal end of the electrode lead directly distal to the plug connector of the electrode lead around the electromedical implant and stores it with the device in the tissue pocket provided therefore.

This method has a few disadvantages which can definitely interfere with the reliable function of the electromedical implant and the related diagnostics and/or therapy, which can lead to life-threatening states for the patient.

An important disadvantage is that the electromedical implant, as well as the wrapped portions of the electrode lead, are quickly enclosed by endogeneous tissue. As this occurs, tissue penetrates every open space in the tissue pocket, thereby enclosing the wrapped portion of the electrode lead.

Consequently, every time a physician replaces the electromedical implant when it has reached the end of its service life, e.g., due to the limited energy capacity, he must cut the wound-up portions of the electrode lead free in order to expose the electromedical device and replace it. In so doing, there is a risk that the sharp-edged dissection instruments will damage the insulation of the electrode lead, thereby exposing connecting lines or creating short circuits between the connecting lines. This can result in erroneous measurements being performed and, therefore, incorrect therapies being administered, which can lead to life-threatening states for the patient.

Furthermore, if the portions of the electrode lead are stored in a disadvantageous manner, the electrode leads can bunch up unfavorably and result in an increased accumulation of material at certain sites, which is uncomfortable for the patient. At these sites, pressure may also be exerted onto the surrounding tissue in a punctiform manner, thereby causing irritation and, in the worst case, inducing inflammatory responses or necrotic states of the adjacent tissue.

This material accumulation caused by the portions of the electrode lead being stored in a disadvantageous manner may also eventually damage the electrode lead. When adhesion occurs, pressure increases on the individual connecting lines, thereby causing a particular squeezing or fulling at certain points since the connecting lines are unable to move to escape the pressure. The elongated, insulating body can become damaged as a consequence. This can likewise result in short circuits or misdiagnoses and incorrect therapies.

Another disadvantage is that, if the electrode lead portions are stored in a disadvantageous manner, they can rub against each other, which can also cause damage.

A solution to these problems is not known from the prior art. A problem therefore to be solved is thus that of creating an implantable device that avoids the stated disadvantages and provides the physician with a storage aid.

The present inventive disclosure is directed toward overcoming one or more of the above-identified problems.

SUMMARY

One or more problems are solved by an implantable device having the features of the independent claim(s). Further advantageous developments are the subject matter of the dependent claims.

According to a first aspect, an implantable device for the reversible accommodation of an electrode lead portion of at least one electrode lead is described, which comprises a first outer surface and a second outer surface which extends parallel to the first outer surface at a distance therefrom, the first outer surface having at least one guide which can be used to guide and accommodate the electrode lead portion. Preferably the distance between the two outer surfaces is substantially smaller than the extension of the outer surface, and is preferably between 0.5 mm and 10 mm. Other distances are also contemplated. It is thereby ensured that the device can be easily stored next to the electromedical implant in the tissue pocket without requiring too much space. The size of the device also simplifies handling for the physician. Instead of storing the electrode lead portions in the tissue pocket in a disorderly manner as before, he can now store them in the guide in an orderly manner and thereby greatly simplify replacement of the electromedical implant.

The at least one guide of the implantable device can be integrated—preferably embedded or recessed—into the first outer surface such that the at least one electrode lead portion does not extend beyond the first outer surface. The electrode lead portions are thereby prevented from exerting pressure on the tissue and thereby inducing inflammation or necrotic states, for example.

According to a first development, the at least one guide extends around an axis which is normal to the first outer surface, thereby enabling the at least one electrode lead portion in the guide to be wound around the axis. In other words, the guide is formed by recesses in the first outer surface, the width of which is less than the distance between the first outer surface and the second outer surface. The guide generally extends in a curve around an imaginary axis, thereby enabling the electrode lead portions to be wrapped around the remainder of the first outer surface. This can also mean that the guide covers the largest portion of the device, while the rest of the outer surface covers a smaller portion of the device. The remainder of the outer surface, being designed as a recess, extends outwardly, i.e., the at least one guide and the outer surface are situated at different heights relative to the second outer surface. As a result, the guidance of the electrode lead portions is simplified even further.

In this first development, the guides are preferably shaped such that they enclose the first outer surface in a shape that is circular, non circular constant diameter type, oval, or octagonal, with rounded corners, thereby resulting in a generally cylindrical formation. The cylindrical formation is created in that the at least one guide is formed as a recess and extends about the imaginary axis. Damage to the electrode lead portion is thereby prevented or minimized, since there are no edges or corners on which the insulating material of the elongated body of the electrode lead portion can become damaged.

More preferably, the guide—in conjunction with this development of the implantable device—comprises cavities that extend laterally at least partially into the first outer surface to prevent the at least one electrode lead portion from slipping. Sections of the first outer surface situated over the guide are thereby produced and prevent the electrode lead portions from slipping out of the guide, which would result in a greater accumulation of material.

In one embodiment, the implantable device according to the first development also comprises a circumferential outer edge that limits the device, the circumferential outer edge being adapted to the outer contour of an electromedical implant. The fit into the tissue pocket is thereby simplified and installation space is optimized. It is also feasible for the implantable device to be reversibly attachable to the electromedical implant, in order to prevent the device from slipping relative to the electromedical implant during use, and to simultaneously enable detachment when replacing the electromedical implant. Such methods for attachment can be implemented, e.g., using clips on the second outer surface, which can be used to clip the device to the electromedical implant. Another method for attachment would be, e.g., to apply a detachable bonding agent to the second outer surface, which can be used to snap the device into place on the electromedical implant.

According to a second development of the implantable device, the at least one guide is integrated, preferably embedded or recessed, as a preformed track into the first outer surface in which the at least one electrode lead portion can be accommodated. As a result, an elongated recess is formed in the first outer surface, which is sized such that the at least one electrode lead portion is guided such that it extends beyond the first outer surface only barely or not at all. According to this embodiment as well, the first outer surface can be hollowed out at least partially on the side to prevent the at least one electrode lead portion from slipping.

The preformed track in the second embodiment is preferably designed and integrated—preferably embedded or recessed—in the first outer surface such that it extends only once at every point of the first outer surface. As a result, the at least one electrode lead portions are prevented from lying on top of one another. As an alternative, the preformed track is designed and integrated—preferably embedded or recessed—in the first outer surface such that the track has recesses at points at which the at least one electrode lead portion passes over itself multiple times. Inflammatory or necrotic state changes of the surrounding tissue are thereby prevented or minimized, since the electrode lead portions do not extend beyond the first outer surface. The electrode lead portions are also prevented from rubbing against each other.

In one embodiment, the implantable device according to the second development also comprises a circumferential outer edge that limits the device, the circumferential outer edge being adapted to the outer contour of an electromedical implant. The fit into the tissue pocket is thereby simplified and installation space is optimized. It is also feasible for the implantable device to be reversibly attachable to the electromedical implant, in order to prevent the device from slipping relative to the electromedical implant during use, and to simultaneously enable detachment when replacing the electromedical implant. Such methods for attachment can be implemented, e.g., using clips on the second outer surface, which can be used to clip the device to the electromedical implant. Another method for attachment would be, e.g., to apply a detachable bonding agent to the second outer surface, which can be used to snap the device into place on the electromedical implant.

The first and the second developments of the implantable device can be made preferably of a hard, non-moldable material or of a soft, deformable material. For example, it can be polypropylene, polyethylene, polyvinyl chloride, polymethylmethacrylate, polymethylmethacrylate, polytetrafluorethylene, polyvinyl alcohol, polyurethane, polybuthylene terephthalate, silicones, polyphosphazene, and the copolymers and blends thereof, although preferably epoxide resin or polypropylene are contemplated as the hard materials, and, e.g., silicone is contemplated as the soft material. Particularly preferably is that the hard or soft material is biodegradable or bioresorbable, wherein the biodegradable or bioresorbable material is, particularly preferably, a biodegradable metal alloy such as, for example, a magnesium or iron alloy, a biodegradable polymer such as polydioxanone, polyglycolide, polycaprolactone, polylactic acid [poly-L-lactide, poly(D,L-lactide)], a copolymers and blends such as, for example, poly(L-lactide-co-glycolide), poly(D,L-lactide-co-glycolide), poly(L-lactide-co-D,L-lactide), poly(l-lactide-co-trimethylene carbonate, triblock copolymers), polysaccharides (chitosan, levan, hyaluronic acid, heparin, dextrane, cellulose, etc.), polyhydroxyvalerate, polyhydroxibutyric acid, ethylvinylacetate, polyethylene oxide, polyphosphorylcholin, fibrin, albumin, or silicone.

In addition, the device according to both developments can be provided with one or more pharmaceutically active substances. A "pharmaceutically active substance" according to the presently disclosed invention is a plant-based, animal-based, or synthetic active agent that is used in suitable doses as a therapeutic agent to influence states or functions of the body, as a replacement for active agents that are produced naturally by human or animal bodies, and to eliminate or render harmless pathogens or foreign substances. The release of the pharmaceutically active substance into the surroundings around the implant has a positive effect on the healing process or counteracts pathological changes in the tissue after the surgical procedure. These pharmaceutically active substances can be integrated or incorporated into the device made of the above-named biodegradable polymer materials, or can be present on the device as a coating, e.g., in an active coating composed of one of the above-named polymer materials.

The pharmaceutically active substances can be, e.g., antiproliferative, antiinflammatory, and/or antimycotic active agents selected from the following non-exhaustive list:

Abciximab, acemetacin, acetylvismione B, aclarubicin, ademetionine, adriamycin, aescin, afromoson, akagerine, aldesleukin, amidorone, aminoglutethemide, amsacrine, anakinra, anastrozole, anemonin, anopterine, antimycotics, antithrombotics, apocymarin, argatroban, aristolactam-A11, aristolochic acid, ascomycin, asparaginase, aspirin, atorvastatin, auranofin, azathioprine, azithromycin, baccatine, bafilomycin, basiliximab, bendamustine, benzocaine, berberine, betulin, betulinic acid, bilobol, biolimus, bisparthenolidine, bleomycin, bombrestatin, Boswellic acids and derivatives thereof, bruceanoles A,B and C, bryophyllin A, busulfan, antithrombin, bivalirudin, cadherins, camptothecin, capecitabine, ocarbamoylphenoxyacetic acid, carboplatin, carmustine, celecoxib, cepharantin, cerivastatin, CETP inhibors, chlorambucil, chloroquine phosphate, cictoxin, ciprofloxacin, cisplatin, cladribine, clarithromycin, colchicine, concanamycin, coumadin, C-type Natriuretic Peptide (CNP), cudraisoflavone A, curcumin, cyclophosphamide, cyclosporine A, cytarabine, dacarbazine, daclizumab, dactinomycin, dapson, daunorubicin, diclofenac, 1,11-dimethoxycanthin-6-one, docetaxel, doxorubicin, daunomycin, epirubicin, epothilones A and B, erythromycin, estramustine, etoposide, everolimus, filgrastim, fluroblastin, fluvastatin, fludarabine, fludarabine-5'-dihydrogenphosphate, fluorouracil, folimycin, fosfestrol, gemcitabine, ghalakinoside, ginkgol, ginkgolic acid, glycoside 1a, 4-hydroxyoxycyclophosphamide, idarubicin, ifosfamide, josamycin, lapachol, lomustine, lovastatin, melphalan, midecamycin, mitoxantrone, nimustine, pitavastatin, pravastatin, procarbazin, mitomycin, methotrexate, mercaptopurine, thioguanine, oxaliplatin, irinotecan, topotecan, hydroxycarbamide, miltefosine, pentostatin, pegasparase, exemestane, letrozole, formestane, SMC proliferation inhibitor-2ω, mitoxanthrone, mycophenolate mofetil, c-myc antisense, [beta]-myc antisense, [beta]-lapachone, podophyllotoxin, podophyllic acid 2-ethylhydrazide, molgramostim (rhuGM-CSF), peginterferon [alpha]-2b, lanograstim (r-HuG-CSF), macrogol, selectin (ctokine antagonist), cytokine inhibitors, COX-2 inhibitor, NFkB, angiopeptin, monoclonal antibodies which inhibit muscle cell proliferation, bFGF antagonists, probucol, prostaglandins, 1-hydroxy-11-methoxycanthin-6-one, scopolectin, NO donors such as pentaerythritol tetranitrate and sydnonimines, S-nitrosoderivatives, tamoxifen, staurosporine, [beta]-estradiol, [alpha]-estradiol, estriol, estrone, ethinylestradiol, medroxyprogesterone, estradiol cypionates, estradiol benzoates, tranilast, kamebakaurin and other terpenoids which are used to treat cancer, verapamil, tyrosine kinase inhibitors (tyrphostins), paclitaxel and derivatives thereof such as 6-[alpha]-hydroxy-paclitaxel, taxotere, macrocyclic oligomers of carbonic suboxide (MCS), mofebutazone, lonazolac, lidocaine, ketoprofen, mefenamic acid, piroxicam, meloxicam, penicillamine, hydroxychloroquine, sodium aurothiomalate, oxaceprol, [beta]-sitosterin, myrtecaine, polidocanol, nonivamide, levomenthol, ellipticine, D-24851 (Calbiochem), colcemid, cytochalasin A-E, indanocine, nocadazole, S 100 protein, bcitracin, vitronectin receptor antagonists, azelastine, guanidyl cyclase stimulator tissue inhibitor of metal proteinase-1 and -2, free nucleic acids, nucleic acids incorporated into virus transmitters, DNA and RNA fragments, plaminogen activator inhibitor-1, plasminogen activator inhibitor-2, antisense oligonucleotides, VEGF inhibitors, IGF-1, active agents from the group of antibiotics cefadroxil, cefazolin, cefaclor, cefotixin tobramycin, gentamycin, penicillins and dicloxacillin, oxacillin, sulfonamides, metronidazole, enoxaparin, desulphated and N-reacetylated heparin (Hemoparin<(R)>), tissue plasminogen activator, GpIIb/IIIa platelet membrane receptor, factor Xa inhibitor antibody, heparin, hirudin, r-hirudin, PPACK, protamine, prourokinase, streptokinase, warfarin, urokinase, vasodilators such as dipyramidol, trapidil, nitroprussides, PDGF antagonists such as triazolopyrimidine and seramine, ACE inhibitors such as captopril, cilazapril, lisinopril, enalapril, losartan, thioprotease inhibitors, prostacyclin, vapiprost, interferon [alpha], [beta] and [gamma], histamine antagonists, serotonin blockers, apoptosis inhibitors, apoptosis regulators such as p65, NF-kB or Bcl-xL antisense oligonucleotides, halofuginone, nifedipine, tocopherol, tranilast, molsidomine, tea polyphenols, epicatechin gallate, epigallocatechin gallate, leflunomide, etanercept, sulfasalazine, etoposide, dicloxacyllin, tetracycline, triamcinolone, mutamycin, procainimide, retinoic acid, quinidine, disopyrimide, flecainide, propafenone, sotolol, natural and synthetically obtained steroids such as inotodiol, maquiroside A, ghalakinoside, mansonine, strebloside, hydrocortisone, betamethasone, dexamethasone, non-steroidal substances (NSAIDS) such as fenoprofen, ibuprofen, indomethacin, naproxen, phenylbutazone, and other antiviral agents such as acyclovir, ganciclovir and zidovudin, clotrimazole, flucytosine, griseofulvin, ketoconazole, miconazole, nystatin, terbinafine, antiprotozoal agents such as chloroquine, mefloquine, quinine, and other natural terpenoids such as hippocaesculin, barringtogenol-C21-angelat, 14-dehydroagrostistachin, agroskerin, agrostistachin, 17-hydroxyagrostistachin, ovatodiolids, 4,7-oxycycloanisomel acid, baccharinoids B1, B2, B3 and B7, tubeimoside, bruceantinoside C, yadanziosides N and P, isodeoxyelephantopin, tomenphantopin A and B, coronarin A,B,C and D, ursolic acid, hyptatic acid A, isoiridogermanal, maytenfoliol, effusantin A, excisanin A and B, longikaurin B, sculponeatin C, kamebaunin, leukamenin A and B, 13,18-dehydro-6-alpha-senecioyloxychaparrin, taxamairin A and B, regenilol, triptolide, and cymarin, hydroxyanopterin, protoanemonin, cheliburin chloride, sinococuline A and B, dihydronitidine, nitidine chloride, 12-betahydroxypregnadiene-3, 20-dion, helenalin, indicine, indicine-N-oxide, lasiocarpine, inotodiol, podophyllotoxin, justicidin A and B, larreatin, malloterin, mallotochromanol, isobutyrylmallotochromanol, maquiroside A, marchantin A, maytansin, lycoridicin, margetine, pancratistatin, liriodenine, bisparthenolidine, oxoushinsunine, periplocoside A, ursolic acid, deoxypsorospermin, psycorubin, ricin A, sanguinarine, manwu what acid, methylsorbifolin, sphatheliachromen, stizophyllin, mansonine, streblo side, dihydrousambaraensine, hydroxyusambarine, strychnopentamine, strychnophylline, usambarine, usambarensine, liriodenine, oxoushinsunine, daphnoretin, laricires-inol, methoxylariciresinol, syringaresinol, sirolimus (rapamycin), somatostatin, tacrolimus, roxithromycin, troleandomycin, simvastatin, rosuvastatin, vinblastine, vincristine, vindesine, teniposide, vinorelbine, tropfosfamide, treosulfan, tremozolomide, thiotepa, tretinoin, spiramycin, umbelliferone, desace-tylvismione A, vismione A and B, zeorin.

Preferably, the active agents belong to the classes glucocorticoids and/or aminoglycoside antibiotics, such as, for example, dexamethasone or gentamicin integrated in a poly (D,L-lactide) coating. Other classes are also contemplated.

According to a second aspect, an electromedical implant is described, in the case of which the implantable device is integrated into the housing thereof. In that case, the electromedical implant comprises the above-described device and an electronic circuit with a power supply, a multipiece housing which hermetically seals the circuit and the power supply, and a connector housing which is fastened to the multipiece, hermetically sealed housing and has connectors for at least one electrode lead, the connectors being electrically connected to the electronic circuit. The electromedical implant is characterized in that the second outer surface of the device forms a part of the housing. Preferably the first outer surface and the at least one guide are accessible from the outside. This embodiment further prevents damage to the tissue pocket. Furthermore, this aspect combines all of the advantages described above.

Various other objects, aspects and advantages of the present inventive disclosure can be obtained from a study of the specification, the drawings, and the appended claims.

DESCRIPTION OF THE DRAWINGS

The subject matter of the application is described in the following with reference to figures. They show.

DETAILED DESCRIPTION

Figure 1A:
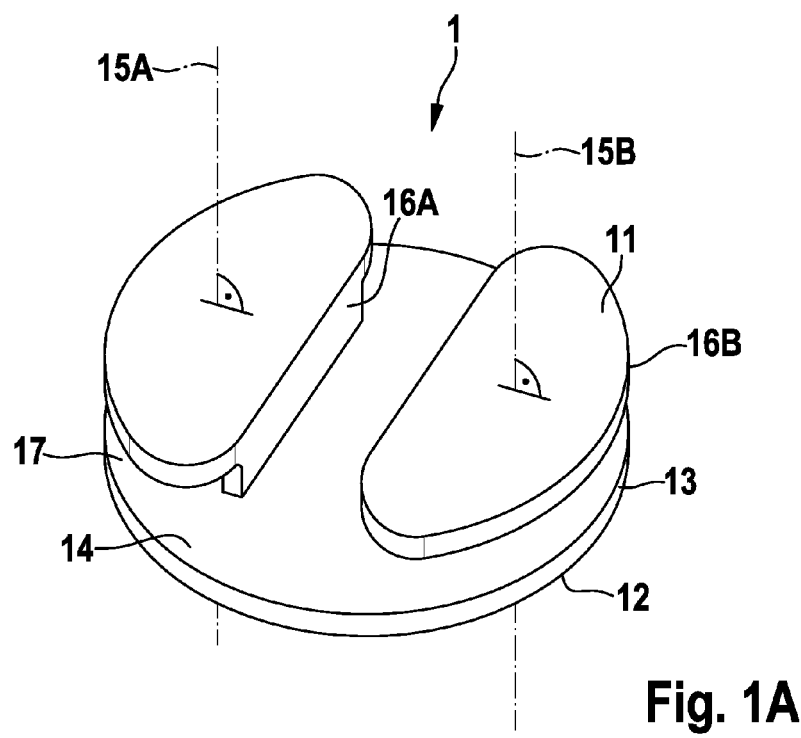
FIGS. 1A-1C show an implantable device according to a first development of a first and second aspect, in which the guide are disposed around two imaginary axes.
Figure 1B:
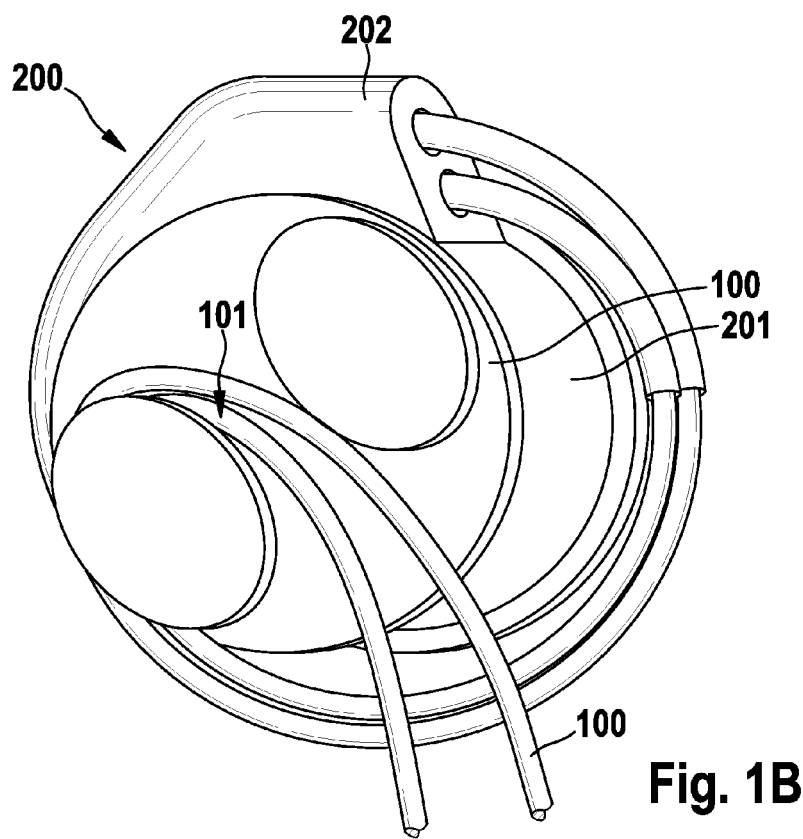
Figure 1C:
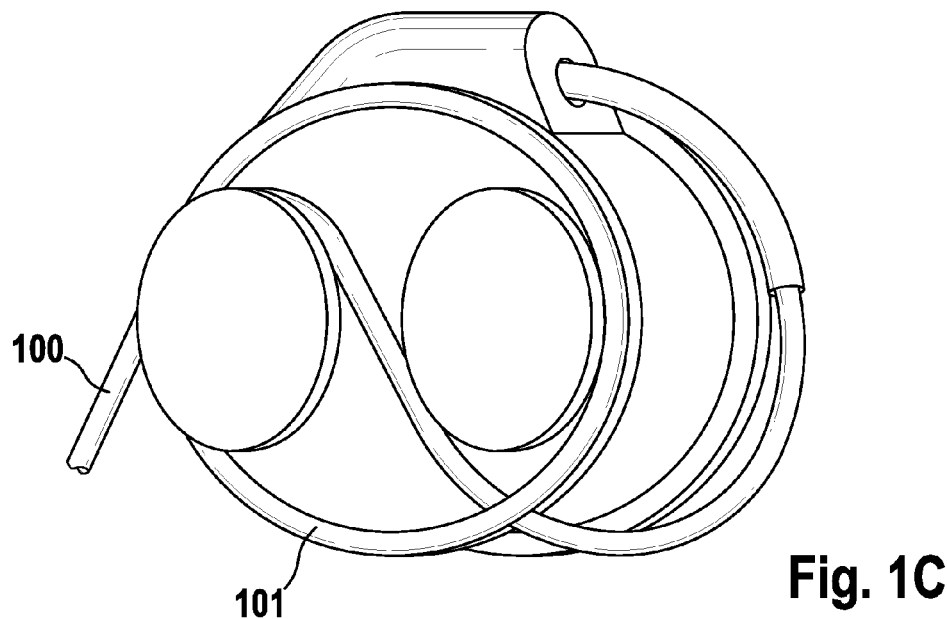

FIGS. 1A-1C show an implantable device 1 having a first outer surface 11 and a second outer surface 12 which is opposite the first outer surface 11 and extends parallel thereto. Outer surface 12 is not visible in these perspective depictions. The device 1 is limited by a circumferential outer edge 13.

A guide 14 is integrated in first outer surface 11, and embedded in first outer surface 11 in this case. As a result, the guide 14 is situated at a height that is lower than that of the first outer surface 11. In this development of the first aspect, guide 14 extends around two imaginary axes 15A and 15B, thereby forming two generally cylindrical formations 16A and 16B, about which one or more electrode lead portions 101 of one or more electrode leads 100 can be wrapped, as shown in FIGS. 1B-1C.

As shown as an example, the height of cylindrical formation 16A or 16B is at least so high that electrode lead portion 101 extends above the cylindrical formation only barely or not at all. Cylindrical formation 16B has a height that corresponds approximately to the diameter of electrode lead portion 101. However, cylindrical formation 16A is so high that a lateral recess 17 can be formed. Recess 17 has a height that is slightly greater than the diameter of electrode lead portion 101. Electrode lead portion 101 can therefore be guided into recess 17, thereby preventing the electrode from slipping or becoming detached from the implantable device 1. The depth of recess 17 can be selected such that two or more electrode leads 100 can be placed therein. This is shown in FIG. 1B as an example.

As an alternative or in addition thereto, it is also feasible to use fixation means to affix electrode lead portions 101 to implantable device 1. Biocompatible kneading mixtures, for instance, i.e., biocompatible polymers (such as, for example, those listed above) having softening temperatures of approximately 37° C. or below (which can be set or provoked, e.g., in the granulation process before an extrusion), or thermoplastically deformable silicone can be used for this purpose. It is also possible, for example, to fasten a foil or a very thin sheet onto first outer surface 11 from above, e.g., in a reversible manner, as described above. This covering can also cover outer edge 13. Entire electrode lead portion 101 is therefore enclosed and protected against adhesion.

Due to the planar design thereof, the implantable device 1 can be placed into the tissue pocket containing the electromedical implant. FIG. 1B shows that implantable device 1 of the type described above can also be placed on an electromedical implant 200. Implant 200 generally comprises a housing 201, which is typically formed of two or more pieces and is comprised of a conductive material such as, for example, titanium, and a connector housing 202 which is comprised of a non-conductive plastic. Sockets are located inside the connector housing, to receive the plugs located on the proximal end of the electrode lead. The sockets have contact surfaces which are also connected to an electronic circuit supplied by a power supply (not shown). Implantable device 1 can be connected on second outer surface 12 to housing 201 of electromedical implant 200. It is important to design the connection to be detachable so that the electromedical implant 200 can be easily replaced once it reaches the end of its service life. This connection can be formed, e.g., using detachable bonding agents. To replace electromedical implant 200, the physician can therefore open the tissue pocket, remove the plugs of electrode leads 100 from the sockets, remove implantable device 1 from housing 201 of the electromedical implant, insert the new electromedical implant, refasten the implantable device 1 to the housing of the new electromedical implant, and restore the electrical contact to the electrode lead by inserting the plugs into the sockets.

According to a second aspect, the implantable device as shown in FIG. 1C can also be integrated into housing 201 of the electromedical implant 200. To this end, the second outer surface forms a part (e.g., a half shell) of the housing 201 which is formed of two or more pieces. In this case, it is necessary to cover electrode lead portions 101 entirely with additional fixation means to prevent electrode lead 100 from adhering to the tissue pocket. The electrode lead 100 can then be cut free easily without becoming damaged.

Figure 2A:
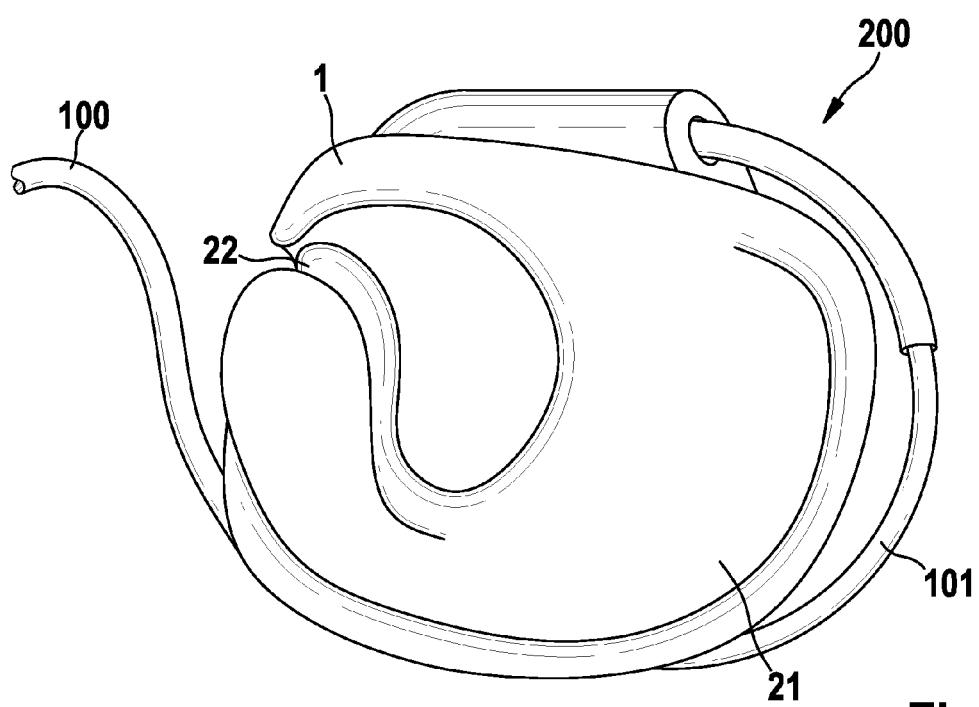
FIGS. 2A-2C show an implantable device according to a second development of the second aspect, in which the guide are designed as tracks.
Figure 2B:
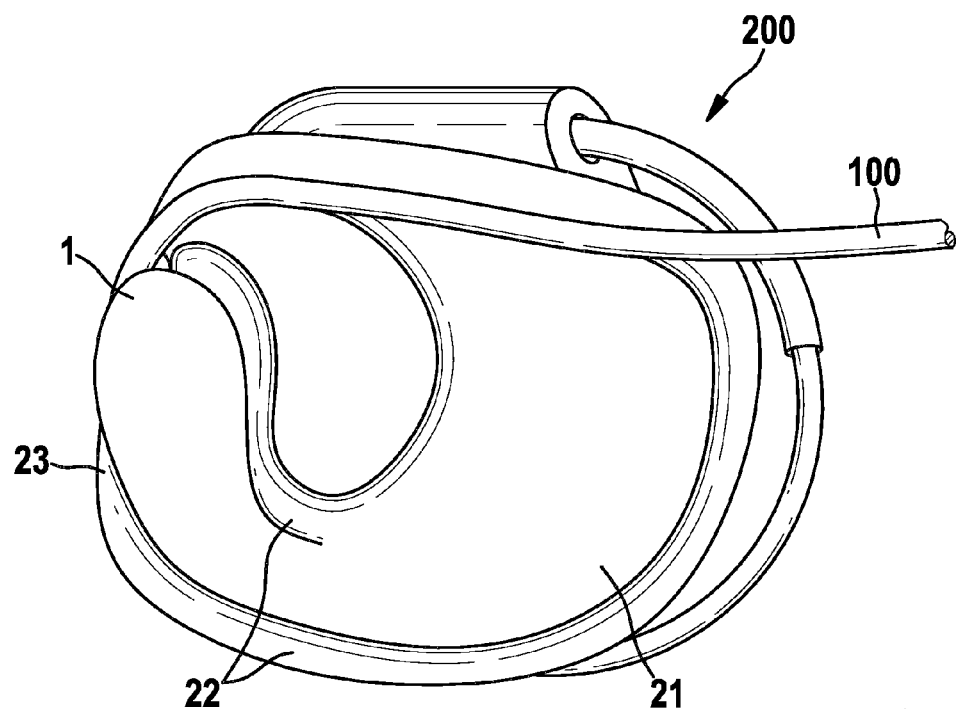
Figure 2C:
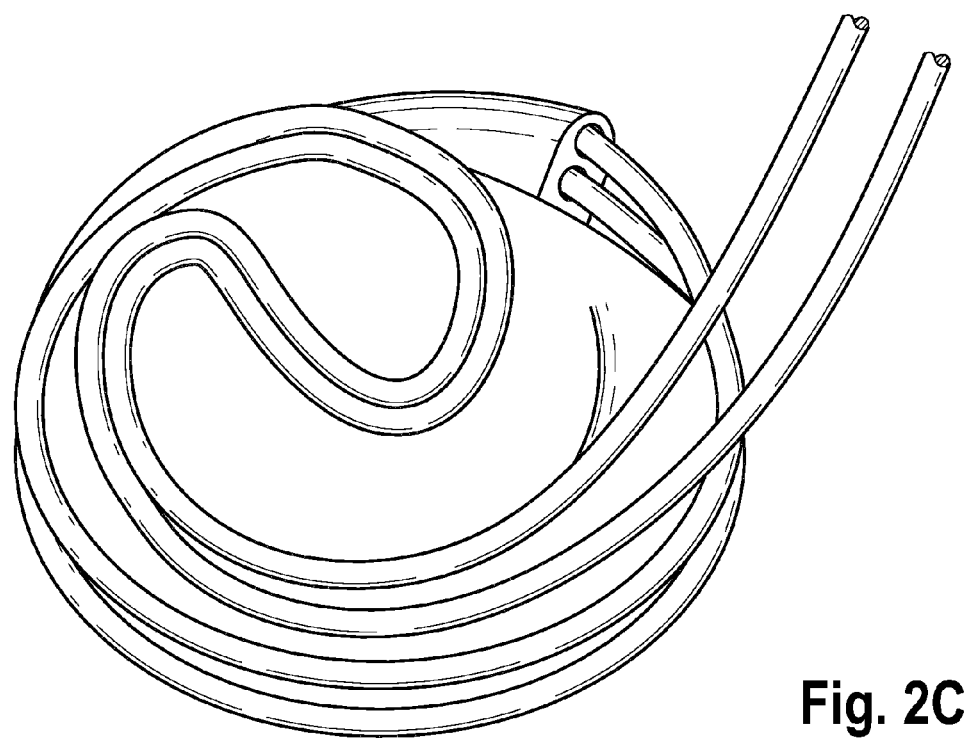

FIGS. 2A-2C show implantable device 1 in a second development, in this case as an integral component of housing 201 of electromedical implant 200. In this case, the guides are a track 22 which is embedded in first outer surface 21. Track 22 may also be enclosed only partially by the outer surface, thereby enabling electrode lead portion 101 to be guided along the outer contour of the electromedical implant 200 when outer edge 23 of implantable device 1 has been adapted to the outer contour. The depth of tracks 22, 23 is selected such that the electrode lead portions 101 barely extend beyond the first outer surface, as in the previously described embodiment. Likewise, tracks 22, 23 can be designed to accommodate one or more electrode lead portions 101.

All of the additional fixation or protection means described above can also be used in this embodiment as well.

A combination of both developments of the implantable device 1 is also feasible. Such a combination is shown in FIG. 1C as an example. In that case, a part of electrode lead portion 101 extends in a track 22 to prevent an excessive amount of material—which would extend beyond first outer surface 11—from accumulating at the point at which two parts of electrode lead portion 101 lie on top of one another. This measure can also be implemented in the second embodiment according to FIGS. 2A-2C.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An implantable device for the reversible accommodation of an electrode lead portion of at least one electrode lead, comprising:
    a first planar outer surface; and
    a second planar outer surface which extends parallel to the first planar outer surface at a distance therefrom,
    wherein the first planar outer surface further comprises first and second cylindrical formations having first and second axes, respectively, extending perpendicular to the first planar outer surface,
    wherein the first cylindrical formation extends from the first planar outer surface by a distance corresponding to a diameter of the electrode lead portion,
    wherein the second cylindrical formation extends from the first planar outer surface such that a recess is formed between the second cylindrical formation and the first planar outer surface, wherein the recess has a height that is greater than the diameter of the electrode lead portion,
    wherein the first and second cylindrical formations and the first planar outer surface are configured to define at least one guide in a lateral recess to guide and accommodate the electrode lead portion within the lateral recess and around the first and second axes, and
    wherein the second planar outer surface of the implantable device forms a part of an outer surface of a housing of the implantable device.

2. The implantable device according to claim 1, wherein a portion of the at least one guide is integrated into the first and second cylindrical formations such that the at least one electrode lead portion does not extend beyond the first and second cylindrical formations.

3. The implantable device according to claim 2, wherein the portion of the at least one guide extends around an axis which is normal to the first outer surface, such that the at least one electrode lead portion in the guide can be wound around the axis.

4. The implantable device according to claim 3, wherein the portion of the at least one guide is shaped such that it encloses the first and second cylindrical formations in a shape selected from the group consisting of circular, non circular constant diameter type, oval, and octagonal with rounded corners, thereby resulting in a cylindrical formation.

5. The implantable device according to claim 3, wherein the portion of the at least one guide comprises cavities that extend laterally at least partially into the first and second cylindrical formations to prevent the at least one electrode lead portion from slipping.

6. The implantable device according to claim 1, further comprising a circumferential outer edge that limits the implantable device, the circumferential outer edge being adapted to an outer contour of an electrical implant.

7. The implantable device according to claim 1, further comprising means on the second outer surface for reversibly attaching the implantable device to an electromedical implant.

8. The implantable device according to claim 1, wherein the implantable device is made of a hard, non-moldable material which is biodegradable or bioresorbable.

9. The implantable device according to claim 8, wherein the biodegradable or bioresorbable material is a biodegradable metal alloy or a biodegradable polymer.

10. The implantable device according to claim 1, wherein the implantable device is made of a soft, deformable material which is biodegradable or bioresorbable.

11. The implantable device according to claim 10, wherein the biodegradable or bioresorbable material is a biodegradable metal alloy or a biodegradable polymer.

12. The implantable device according to claim 1, further comprising one or more pharmaceutically active substances provided on the implantable device.

13. An electromedical implant comprising:
    the implantable device according to claim 1;
    an electronic circuit with a power supply;
    a multipiece housing which hermetically seals the electronic circuit and the power supply; and
    a connector housing which is fastened to the multipiece, hermetically sealed housing and said connector housing further comprises connectors for at least one electrode lead, the connectors being electrically connected to the electronic circuit,
    wherein the second outer surface of the implantable device forms a part of an outer surface of the housing.

14. The electromedical implant according to claim 13, wherein the first and second cylindrical formations and the at least one guide are accessible from an outside of the electromedical implant.

15. The implantable device according to claim 1, further comprising fixation means for affixing the electrode lead portion to the implantable device.

16. The implantable device according to claim 1, further comprising a sheet fastened to the first and second cylindrical formations and extending to the circumferential outer edge, wherein the electrode lead portion is covered by the sheet.

* * * * *